US009993457B2

(12) United States Patent
Kuchan et al.

(10) Patent No.: US 9,993,457 B2
(45) Date of Patent: Jun. 12, 2018

(54) METHOD OF IMPROVING VISUAL PROCESSING, VISUAL ACUITY, OR BOTH BY ADMINISTERING COMPOSITIONS COMPRISING RRR-ALPHA-TOCOPHEROL AND CAROTENOID TO INFANTS

(71) Applicant: ABBOTT LABORATORIES, Abbott Park, IL (US)

(72) Inventors: Matthew Kuchan, Westerville, OH (US); Chron-Si Lai, Blacklick, OH (US); Jacqueline Boff, Dublin, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days. days.

(21) Appl. No.: 15/529,305

(22) PCT Filed: Nov. 25, 2015

(86) PCT No.: PCT/US2015/062667
§ 371 (c)(1),
(2) Date: May 24, 2017

(87) PCT Pub. No.: WO2016/086128
PCT Pub. Date: Jun. 2, 2016

(65) Prior Publication Data
US 2017/0258759 A1 Sep. 14, 2017

Related U.S. Application Data

(60) Provisional application No. 62/084,326, filed on Nov. 25, 2014.

(51) Int. Cl.
*A61K 31/335* (2006.01)
*A61K 31/01* (2006.01)
*A61K 31/07* (2006.01)
*A61K 31/59* (2006.01)
*A61K 31/12* (2006.01)
*A61K 31/20* (2006.01)
*A61K 31/355* (2006.01)
*A23L 33/155* (2016.01)
*A23L 33/12* (2016.01)
*A23L 33/15* (2016.01)
*A23L 33/00* (2016.01)
*A61K 31/015* (2006.01)
*A61K 31/047* (2006.01)

(52) U.S. Cl.
CPC ............ *A61K 31/355* (2013.01); *A23L 33/12* (2016.08); *A23L 33/15* (2016.08); *A23L 33/155* (2016.08); *A23L 33/30* (2016.08); *A23L 33/40* (2016.08); *A61K 31/015* (2013.01); *A61K 31/047* (2013.01); *A23V 2002/00* (2013.01)

(58) Field of Classification Search
CPC ...... A61K 31/335; A61K 31/59; A61K 31/12; A61K 31/20; A01N 61/02
USPC ................ 514/167, 458, 560, 681, 725, 762
See application file for complete search history.

(56) References Cited

U.S. PATENT DOCUMENTS

| | | |
|---|---|---|
| 5,972,985 A | 10/1999 | Thomas et al. |
| 6,254,898 B1 | 7/2001 | Bragaglia |
| 6,294,206 B1 | 9/2001 | Barrett-Reis et al. |
| 6,472,003 B2 | 10/2002 | Barrett-Reis et al. |
| 6,495,599 B2 | 12/2002 | Auestad et al. |
| 6,576,253 B2 | 6/2003 | Manning et al. |
| 6,649,195 B1 | 11/2003 | Gorsek |
| 7,090,879 B2 | 8/2006 | Albrecht et al. |
| 7,351,715 B2 | 4/2008 | Richardson et al. |
| 7,635,469 B2 | 12/2009 | Prasad et al. |
| 7,771,756 B1 | 8/2010 | Schlesser |
| 8,075,934 B2 | 12/2011 | Banavara et al. |
| 8,183,227 B1 | 5/2012 | Perrin et al. |
| 8,263,147 B2 | 9/2012 | Barrett-Reis et al. |
| 8,389,504 B2 | 3/2013 | Debbouz et al. |
| 8,475,849 B2 | 7/2013 | Phillips |

(Continued)

FOREIGN PATENT DOCUMENTS

| | | |
|---|---|---|
| WO | 2013138157 A1 | 9/2013 |
| WO | 2014159967 A1 | 10/2014 |

(Continued)

OTHER PUBLICATIONS

Acuff et al., "Transport of Deuterium-Labeled Tocopherols During Pregnancy," The American Journal of Clinical Nutrition, Mar. 1, 1998, p. 459-464.
Barbin G et al., "Involvement of GABAA Receptor in the Outgrowth of Cultured Hippocampal Neurons," (1993) Neuroscience Letters 152: 150-154.
Birgbauer et al., "New Developments in the Biological Functions of Lysophospholipids," Cell Mol Life Sci, 63 (23), 2695-2701 Dec. 2006.
Chartier, "Feed Your Brain," http://www.naturalproductsmarketplace.com/articles/551/69h110817 . . . , accessed Nov. 12, 2007, 6 pages.
Deng, et al., "Lysophosphatidic Acid Protects and Rescues Intestinal Epithelial Cells From Radiation- and Chemotherapy-Induced Aoptosis," Gastroenterology Jul. 2002;123:206-216.

(Continued)

*Primary Examiner* — Raymond J Henley, III
(74) *Attorney, Agent, or Firm* — Calfee, Halter & Griswold LLP

(57) ABSTRACT

Methods for improving the visual processing of a healthy infant by administering a composition comprising RRR-alpha-tocopherol and a carotenoid to the infant are disclosed. Methods for improving the visual acuity of a healthy infant by administering a composition comprising RRR-alpha-tocopherol and a carotenoid to the infant are also disclosed. Methods for improving the visual processing of a healthy infant by administering a composition comprising RRR-alpha-tocopherol to the infant are disclosed. Methods for improving the visual acuity of a healthy infant by administering a composition comprising RRR-alpha-tocopherol to the infant are also disclosed. Methods for improving the development of the visual processing, visual acuity, or both, of an infant by administering a composition comprising RRR-alpha-tocopherol to the infant are also disclosed.

19 Claims, 3 Drawing Sheets

(56) References Cited

U.S. PATENT DOCUMENTS

| | | |
|---|---|---|
| 8,545,896 B2 | 10/2013 | Perrin et al. |
| 8,697,115 B2 | 4/2014 | Barrett-Reis et al. |
| 8,703,716 B2 | 4/2014 | Zimmer et al. |
| 8,709,515 B1 | 4/2014 | Colitz et al. |
| 2005/0249821 A1 | 11/2005 | Paul |
| 2006/0020046 A1 | 1/2006 | Goralczyk et al. |
| 2006/0057186 A1 | 3/2006 | Heller |
| 2006/0275059 A1 | 11/2006 | Lockwood et al. |
| 2008/0181972 A1 | 7/2008 | Amico et al. |
| 2008/0194417 A1 | 8/2008 | Barella et al. |
| 2009/0118228 A1 | 5/2009 | Jouni et al. |
| 2009/0297625 A1 | 12/2009 | Tikhonov et al. |
| 2010/0233145 A1 | 9/2010 | Van Veen |
| 2011/0136734 A1 | 6/2011 | Barrett-Reis |
| 2011/0189319 A1 | 8/2011 | Leitman et al. |
| 2012/0071550 A1 | 3/2012 | Zelkha et al. |
| 2013/0011377 A1 | 1/2013 | Perrin et al. |
| 2013/0196008 A1 | 8/2013 | Van Elswyk |
| 2014/0005151 A1 | 1/2014 | Lockwood |
| 2014/0010889 A1 | 1/2014 | Minatelli et al. |
| 2014/0023751 A1 | 1/2014 | Perrin et al. |
| 2014/0080767 A1 | 3/2014 | Zimmer et al. |

FOREIGN PATENT DOCUMENTS

| | | |
|---|---|---|
| WO | 2014160335 A1 | 10/2014 |
| WO | 2015073515 A1 | 5/2015 |

OTHER PUBLICATIONS

Fisher, et al., "Inositol and Higher Inositol Phosphates in Neural Tissues: Homeostasis, Metabolism and Functional Significance," J Neurochem. Aug. 2002;82(4):736-754.

Gruszecki, et al., "Carotenoids as Modulators of Lipid Membrane Physical Properties," Biochimica et Biophysica Acta 1740 (2005) 108-115.

Kingsbury, et al. "Non-proliferative Effects of Lysophosphatidic Acid Enhance Cortical Growth and Folding" Nature Neuroscience 6, 1292-1299 (2003).

Lieblein-Boff, et al., "The Naturally Occurring α-Tocopherol Stereoisomer of Vitamin E is Predominant in Infant Brain," Advances and Controversies in Clinical Nutrition 2013 (Abstract, RRT101489).

McNulty et al., "Biologic Activity of Carotenoids Related to Distinct Membrane Physicochemical Interactions," Am J Cardiol 101 (10A), 20D-29D. May 22, 2008.

McNulty et al., "Differential Effects of Carotenoids on Lipid Peroxidation Due to Membrane Interactions: X-ray Diffraction Analysis," Biochimica et Biophysica Acta 1768 (2007) 167-174.

Morell & Norton (1980) Sci Am 242:88-90, 92, 96 passim.

Nagaroli et al., "Lysophosphatidic Acid Can Support the Formation of Membranous Structures and an Increase in MBP mRNA Levels in Differentiating Oigodendrocytes," Neurochem Res. Jan. 2009; 34(1): 182-193.

O'Brien et al., "Lipid Composition of the Normal Human Brain: Gray Matter, White Matter, and Myelin," Oct. 1965 The Journal of Lipid Research, 6, 537-544.

Sherry, et al. Lutein Supplementation Increases Breast Milk and Plasma Lutein Concentrations in Lactating Women and in Infant Plasma Concentrations but Does not Affect Other Carotenoids1-3, The Journal of Nutrition, Jun. 4, 2014, 8 pages.

Smith, et al., "Serum Beta Carotene, Alpha Tocopherol, and Age-Related Maculopathy: the Blue Mountains Eye Study", American Journal of Opthalmology, Dec. 1997, pp. 838-840.

Socaciu C, et al., "Competitive Carotenoid and Cholesterol Incorporation Into Liposomes: Effects on Membrane Phase Transition, Fluidity, Polarity and Anisotropy ." Chem Phys Lipids 106 (1), 79-88. 6 2000.

Sommerburg, et al., "Carotenoid Supply in Breast-Fed and Formula-Fed Neonates," Eur J Pediatr (2000) 159, pp. 86-90.

Sowell et al. "Retinal, α-Tocopherol, Lutein/Zeaxanthin, β-Cryptoxanthin, Lycopene, α-Carotene, trans-β-Carotene, and Four Retinyl Esters in Serum Determined Simultaneously by Reversed-Phase HPLC with Multiwavelength Detection," Clin. Chem. 40/3, 411-416 (1994) Automatic and Analytical Techniques.

Stone, et al., "Infants Discriminate Between Natural and Synthetic Vitamin E 1-4," Am J Clin Nutr, Jan. 1, 2003 pp. 899-906.

Torkhovskaya et al., "Lysophospholipid Receptors in Cell Signaling," Biochemistry (Mosc) 72 (2), 125-13, Feb. 2007.

Vishwanathan et al. "Lutein is the Predominant Carotenoid in Infant Brain: Preterm Infants Have Decreased Concentrations of Brain Carotenoids," JPGN Journal of Pediatric Gastroenterology and Nutrition Publish Ahead of Print, 2014, 26 pages.

International Search Report and Written Opinion from PCT/US2015/062667 dated Feb. 12, 2016.

Wade et al., "A Possible Role for Taurine in Osmoregulation Within the Brain," J Neurochem 51 (3), 740-745. 9 1988.

Wiśniewska, et al., "Is a Fluid-Mosaic Model of Biological Membranes Fully Relevant? Studies on Lipid Organization in Model and Biological Membranes," Cellular & Molecular Biology Letters, vol. 8, (2003) pp. 147-159.

Wiśniewska, et al., "Accumulation of Macular Xanthophylls in Unsaturated Membrane Domains," Free Radic Biol Med 40 (10), 1820-1826. Feb. 3, 2006.

Yung et al., LPA Receptor Signaling: Pharmacology, Physiology, and Pathophysiology, J Lipid Res. Jul. 2014;55 (7):1192-1214.

Written Opinion from Singapore Patent Application No. 11201704161Y dated Mar. 15, 2018.

METHOD OF IMPROVING VISUAL PROCESSING, VISUAL ACUITY, OR BOTH BY ADMINISTERING COMPOSITIONS COMPRISING RRR-ALPHA-TOCOPHEROL AND CAROTENOID TO INFANTS

CROSS-REFERENCE TO RELATED APPLICATIONS

This application is the U.S. national stage entry of International Application No. PCT/US2015/062667, filed Nov. 25, 2015, which claims priority to and any benefit of U.S. Provisional Application No. 62/084,326 filed Nov. 25, 2014, the contents of which are incorporated herein by reference in theft entirety.

FIELD OF THE DISCLOSURE

The present disclosure relates to methods of improving the visual processing, visual acuity, or both in infants, by administering to the infants compositions comprising RRR-alpha-tocopherol, also sometimes called "natural Vitamin E," and, in some embodiments, a carotenoid. The present disclosure also relates to methods of improving the development of visual processing, visual acuity, or both in an infant. The method increases the preferential accumulation of RRR-alpha-tocopherol in the occipital cortex of the infant's brain. The method also reduces the accumulation of non-RRR-alpha-tocopherol stereoisomers in the occipital cortex of the infant's brain.

BACKGROUND OF THE INVENTION

Vitamin E is an antioxidant that is essential for development of the nervous system. The term "Vitamin E" encompasses many classes of chemicals, and the type of Vitamin E best absorbed by humans is alpha-tocopherol. Eight distinct stereoisomers of alpha tocopherol exist, but the only form of alpha-tocopherol found in nature is RRR-alpha-tocopherol. In comparison, synthetic alpha-tocopherol is made of essentially equal amounts of all eight stereoisomers.

It is known that the stereoisomers of alpha-tocopherol differ in their bioavailability, with RRR-alpha-tocopherol being the most bioavailable form. It is also known that, in certain species (e.g., rat), the brain also preferably selects and absorbs RRR-alpha-tocopherol as compared to the seven other stereoisomers.

SUMMARY OF THE DISCLOSURE

Some embodiments of the present disclosure are directed to methods of improving the visual processing of a healthy infant, the method comprising administering a nutritional composition comprising RRR-alpha-tocopherol and a carotenoid to the infant.

Some embodiments of the present disclosure are directed to methods of improving the visual acuity of a healthy infant, the method comprising administering a nutritional composition comprising RRR-alpha-tocopherol and a carotenoid to the infant.

Some embodiments of the present disclosure are directed to methods of improving the visual processing of a healthy infant, the method comprising administering a nutritional composition comprising RRR-alpha-tocopherol to the infant.

Some embodiments of the present disclosure are directed to methods of improving the visual acuity of a healthy infant, the method comprising administering a nutritional composition comprising RRR-alpha-tocopherol to the infant.

Some embodiments of the present disclosure are directed to methods of improving the development of visual processing, visual acuity, or both in an infant, the method comprising administering a nutritional composition comprising RRR-alpha-tocopherol to the infant.

Some embodiments of the present disclosure are directed to methods of improving the development of visual processing, visual acuity, or both in a fetus, the method comprising administering a nutritional composition comprising RRR-alpha-tocopherol to a pregnant woman. Some embodiments of the present disclosure are directed to methods of improving the development of visual processing, visual acuity, or both in a breastfeeding infant, the method comprising administering RRR-alpha-tocopherol to the infant through the breastmilk of a lactating woman by administering a nutritional composition comprising RRR-alpha-tocopherol to the lactating woman. In accordance with embodiments disclosed herein, the nutritional composition administered to the pregnant woman or lactating woman may further comprise a carotenoid.

Some embodiments of the present disclosure are directed to nutritional compositions administered to an infant for use in improving the visual processing of the infant, the nutritional compositions comprising RRR-alpha-tocopherol and a carotenoid.

Some embodiments of the present disclosure are directed to nutritional compositions administered to an infant for use in improving the visual acuity of the infant, the nutritional compositions comprising RRR-alpha-tocopherol and a carotenoid.

Some embodiments of the present disclosure are directed to nutritional compositions administered to an infant for use in improving the visual processing of the infant, the nutritional compositions comprising RRR-alpha-tocopherol and a carotenoid.

Some embodiments of the present disclosure are directed to nutritional compositions administered to an infant for use in improving the visual acuity of the infant, the nutritional compositions comprising RRR-alpha-tocopherol.

Some embodiments of the present disclosure are directed to nutritional compositions administered to an infant for use in improving the development of visual processing, visual acuity, or both in the infant, the nutritional compositions comprising RRR-alpha-tocopherol.

Some embodiments of the present disclosure are directed to the use of a nutritional composition in the manufacture of a medicament for use in improving the visual processing of an infant, the nutritional composition comprising RRR-alpha-tocopherol and a carotenoid.

Some embodiments of the present disclosure are directed to the use of a nutritional composition in the manufacture of a medicament for use in improving the visual acuity of an infant, the nutritional composition comprising RRR-alpha-tocopherol and a carotenoid.

Some embodiments of the present disclosure are directed to the use of a nutritional composition in the manufacture of a medicament for use in improving the visual processing of an infant, the nutritional composition comprising RRR-alpha-tocopherol.

Some embodiments of the present disclosure are directed to the use of a nutritional composition in the manufacture of a medicament for use in improving the visual acuity of an infant, the nutritional composition comprising RRR-alpha-tocopherol.

Some embodiments of the present disclosure are directed to the use of a nutritional composition in the manufacture of a medicament for use in improving the development of visual processing, visual acuity, or both in an infant, the nutritional composition comprising RRR-alpha-tocopherol.

The nutritional composition administered to the infant may be a nutritional product including but not limited to an infant nutritional formula or a vitamin supplement. The infant may be a premature infant. The infant may be a full-term infant. The infant may not have an ocular disease. The nutritional composition administered to the pregnant woman or lactating woman may be a nutritional product including but not limited to a nutritional food product or a vitamin supplement.

DETAILED DESCRIPTION OF THE DISCLOSURE

Figure 1:
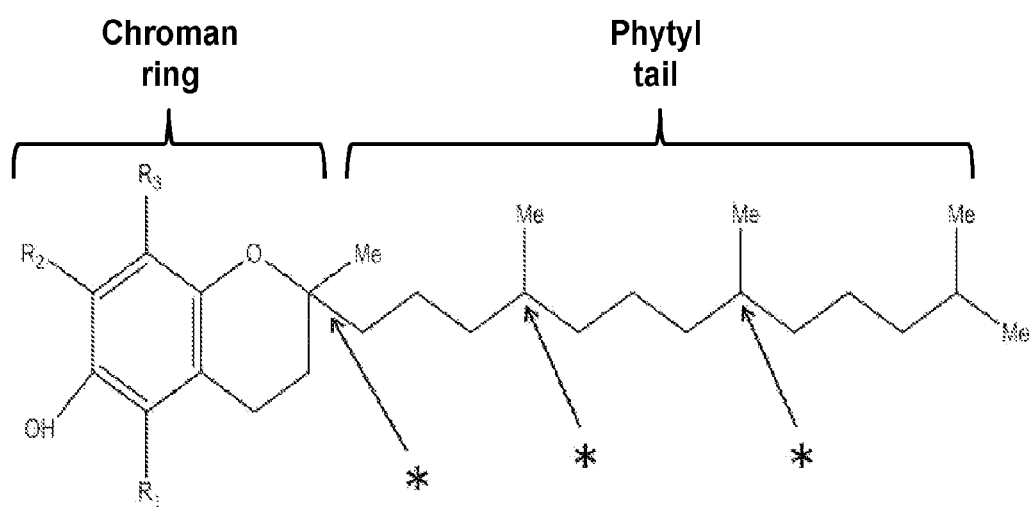
FIG. 1 shows the chemical structure of the tocopherol family.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Vitamin E is essential for development, and deficiency disrupts the central nervous system resulting in neurological disorders. The term "Vitamin E" can encompass two classes of chemicals, tocopherols and tocotrienols. The form of Vitamin E that is best absorbed by humans is alpha-tocopherol, and hence the terms "Vitamin E" and "alpha-tocopherol" are often used interchangeably in medical and non-technical communications.

Alpha-tocopherol is a nutrient found in many vegetable oils such as sunflower oil, safflower oil, and olive oil. Alpha-tocopherol is also found in seeds, nuts, and some vegetables such as spinach. Alpha-tocopherol has three chiral carbons in its chemical structure, which create three centers of asymmetry. This means that eight stereoisomers exist, which are chemically the same but structurally and biologically somewhat different. Natural alpha-tocopherol, as found in foods, is a single stereoisomer, RRR-alpha-tocopherol. However, when alpha-tocopherol is synthetically produced, the manufacturing methods do not preferentially form any specific stereoisomer. Instead, synthetic alpha-tocopherol contains substantially equal amounts of all eight stereoisomers, only one of which is RRR-alpha-tocopherol. In 100 g of synthetic alpha-tocopherol, each stereoisomer constitutes about 12.5 g of the total. Because it is made up of all eight stereoisomers, synthetic alpha-tocopherol is also known as "racemic-" or all-rac-alpha-tocopherol.

It is known that the stereoisomers of alpha-tocopherol differ in their bioavailability, with RRR-alpha-tocopherol being the most bioavailable form. RRR-alpha-tocopherol is preferentially transferred from the liver into very-low-density lipoproteins (VLDL), and then into plasma and red blood cells. Other organs, such as the brain, also preferentially absorb the RRR-alpha-tocopherol stereoisomer over the other stereoisomers in all-rac-alpha-tocopherol. Hence, RRR-alpha-tocopherol is more bioavailable and biologically active than the other stereoisomers because certain metabolic systems of the human body preferentially absorb RRR-alpha-tocopherol over the non-RRR-alpha-tocopherol stereoisomers.

It is also known that rodent brain exerts additional selectivity for RRR-alpha-tocopherol as compared to non-RRR-alpha-tocopherol. However, it has been unclear if selectivity of alpha-tocopherol stereoisomers occurs in human infant brains. The inventors have unexpectedly discovered that RRR-alpha-tocopherol is preferentially accumulated in the brain of infants, and specifically in the occipital cortex of infants. This area of the brain is the area of the brain important for processing visual information. The preferential accumulation of RRR-alpha-tocopherol in the occipital cortex is thought to be important to the development of visual processing, visual acuity, or both in an infant. The preferential accumulation of RRR-alpha-tocopherol in the occipital cortex is also thought to be important to supporting visual processing, visual acuity, or both in an infant.

The inventors have also unexpectedly discovered that carotenoids selectively reduce the accumulation of non-RRR-alpha-tocopherol in the occipital cortex of infants' brains, but not in other areas of the brain, such as the frontal cortex or hippocampus.

By administering an infant a nutritional composition comprising RRR-alpha-tocopherol (instead of all-rac-alpha-tocopherol) and a carotenoid, the concentration of RRR-alpha-tocopherol in the occipital cortex of the infant's developing brain is enhanced and the concentration of non-RRR-alpha-tocopherol is reduced. By enhancing the concentration of RRR-alpha-tocopherol and reducing the concentration of non-RRR-alpha-tocopherol in the occipital cortex of an infant's brain, it is thought that the visual processing, visual acuity, or both in the infant can be improved. By enhancing the concentration of RRR-alpha-tocopherol in the occipital cortex of an infant's brain, it is thought that the development of the visual processing, visual acuity, or both is enhanced in the infant.

These and other elements or limitations of the nutritional compositions and methods of making them are described in further detail below.

For the purpose of the present disclosure, the following terms are defined:

The term "infant" as used herein refers to human babies between birth and about 18 months of age.

The term "nutritional composition" refers to the components or ingredients used in a product that is consumed to provide nutrients (e.g., vitamins, pro-vitamins, minerals, macronutrients, etc.). A nutritional composition includes but is not limited to the active ingredients (e.g., RRR-alpha-tocopherol and carotenoid), flavors, colorants, and excipients such as carrier oils or inert solids. In some embodiments, the nutritional composition may include macronutrients (e.g., protein, carbohydrate, or fat) or other optional ingredients (e.g., vitamins or minerals), as discussed below.

The term "infant nutritional composition" as used herein refers to nutritional products ingested by an infant. In some embodiments, the infant nutritional compositions of the present disclosure are infant nutritional formulas.

The terms "improve" and "improving" as used herein refer to providing an adequate source of RRR-alpha-tocopherol and, in certain exemplary embodiments, a carotenoid to an infant, to allow the proper development of the functions of visual processing, visual acuity, or both in the occipital cortex of the infant.

The term "visual processing" as used herein refers to how the brain interprets visual information, i.e., the sequence of steps the brain takes to recognize, identify, and give meaning to visual information.

The term "visual acuity" as used herein refers to the clarity of vision, i.e., how well the eye, retina, optic nerve, and occipital cortex transmit and receive visual information into the brain.

The term "RRR-alpha-tocopherol," which is sometimes referred to as "natural Vitamin E," is used to refer to the stereoisomer of alpha-tocopherol which is found naturally in foods. RRR-alpha-tocopherol comprises about 12.5% of the alpha-tocopherol found in all-rac-alpha-tocopherol. RRR-alpha-tocopherol may come from natural or synthetic sources.

The term "non-RRR-alpha-tocopherol" as used herein refers to any or all of the seven stereoisomers of alpha-tocopherol that are not RRR-alpha-tocopherol. Specifically, non-RRR-alpha-tocopherol includes any one of, any combination of, or all of the alpha-tocopherol stereoisomers RRS-alpha-tocopherol, RSR-alpha-tocopherol, RSS-alpha-tocopherol, SRR-alpha-tocopherol, SRS-alpha-tocopherol, SSR-alpha-tocopherol, and SSS-alpha-tocopherol.

The term "2S-alpha-tocopherol" as used herein refers to any or all of the four stereoisomers of alpha-tocopherol that have an "S" stereocenter carbon at the 2 position on the chroman ring. Specifically, 2S-alpha-tocopherol includes any one of, any combination of, or all of the alpha-tocopherol stereoisomers SRR-alpha-tocopherol, SRS-alpha-tocopherol, SSR-alpha-tocopherol, and SSS-alpha-tocopherol. The 2S-alpha-tocopherol stereoisomers are found only in synthetic Vitamin E.

The term "all-rac-alpha-tocopherol," which is sometimes referred to as "synthetic Vitamin E," is used to refer to a blend of all eight stereoisomers of alpha-tocopherol in substantially equimolar amounts, i.e., each stereoisomer comprises about 12.5% of the total amount of alpha-tocopherol.

The term "carotenoid" as used herein refers to any chemical in a class of organic pigments that are tetraterpenoids. Examples of carotenoids include α-carotene, β-carotene, γ-carotene, lycopene, lutein, zeaxanthin, astaxanthin, α-cryptoxanthin, β-cryptoxanthin, and similar chemicals.

The terms "tissue" or "body tissue" as used herein refer to the organs and fluids contained within or generated by the human body. Tissues include, but are not limited to, organs such as the brain, central nervous system, liver, gastrointestinal tract, and body fluid such as blood and lymph.

The term "bioavailable" or "bioavailability" as used herein, unless otherwise specified, refers to the amount of a nutrient made available to target tissues in the human body through the systemic circulation in the body. In this context, the term "bioavailable" or "bioavailability" may specifically refer to the ability of a nutrient to transfer from the digestive tract into the lymphatic system or bloodstream of an individual and then into the organs and tissues of the body. As the degree of bioavailability of a nutrient increases, the nutrient becomes more likely to enter into and remain in the lymphatic system or bloodstream where it can be absorbed and used by the organs and tissues of the body. As the degree of bioavailability of a nutrient decreases, the nutrient becomes more likely to be excreted from the body before entering the lymphatic system or bloodstream.

The term "capsule" as used herein refers to a dosage element used to deliver a predetermined amount of a nutritional composition to a recipient, wherein the capsule comprises a shell surrounding and containing the nutritional composition. Capsules include, but are not limited to, hard gelatin capsules, starch capsules, cellulose-based capsules, and softgel capsules.

The term "tablet" as used herein refers to a dosage element used to deliver a predetermined amount of a nutritional composition to a recipient, wherein the tablet is a compressed solid mixture comprising the nutritional composition and, typically, a solid excipient such as starch or sugar. The tablet is of an appropriate size and shape to be easily swallowed by the recipient. The tablet may be swallowed whole or, where appropriate, may be swallowed after being chewed by the recipient.

The term "chewable soft gel" as used herein refers to a dosage element used to deliver a predetermined amount of a nutritional composition to a recipient, wherein the chewable soft gel comprises the nutritional composition contained within a gummy gelatin or gelatin-like matrix. The chewable soft gel typically has a pleasant flavor and is designed to be chewed before being swallowed by the recipient.

The term "syrup" as used herein refers to a dosage element used to deliver a predetermined amount of a nutritional composition to a recipient, wherein the syrup comprises the nutritional composition in an aqueous liquid solution, suspension, or emulsion.

The term "elixir" as used herein refers to a dosage element used to deliver a predetermined amount of a nutritional composition to a recipient, wherein the elixir comprises the nutritional composition in an ethanol-based liquid solution, suspension, or emulsion.

All percentages, parts, and ratios as used herein are by weight of the total composition, unless otherwise specified. All such weights as they pertain to listed ingredients are based on the active level, and therefore do not include solvents or by-products that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

The various embodiments of the nutritional compositions of the present disclosure may also be substantially free of any optional or selected essential ingredient or feature described herein, provided that the remaining composition still contains all of the required ingredients or features as described herein. In this context, and unless otherwise specified, the term "substantially free" means that the selected compositions contain less than a functional amount of the optional ingredient, typically less than 0.1% by weight, and also includes zero percent by weight of such optional or selected essential ingredient.

The nutritional compositions and corresponding manufacturing methods of the present disclosure can comprise, consist of, or consist essentially of the essential elements of the disclosure as described herein, as well as any additional or optional element described herein or which is otherwise useful in nutritional composition applications.

To the extent that the terms "includes," "including," "contains," or "containing" are used in the specification or the claims, they are intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

Tocopherols

Tocopherols are a family of related chemicals comprising a chroman ring and a phytyl tail, conforming to the chemical structure shown in FIG. 1.

Tocopherols are available in four forms, alpha, beta, gamma, and delta, which differ in the number and position of the methyl ("Me") groups on the chroman ring (see Table 1 below). Alpha-tocopherol is the tocopherol most commonly referred to as "Vitamin E," and is the best known and most studied of the tocopherol family. However, the beta, gamma, and delta forms of tocopherol may also provide Vitamin E-type properties in the human body, and the American diet actually contains more gamma-tocopherol than alpha-tocopherol.

TABLE 1

| Compound | $R_1$ | $R_2$ | $R_3$ |
| --- | --- | --- | --- |
| alpha-tocopherol | Me | Me | Me |
| beta-tocopherol | Me | H | Me |
| gamma-tocopherol | H | Me | Me |
| delta-tocopherol | H | H | Me |

Tocopherols can exist in a number of stereoisomeric forms because of the three chiral carbons in the molecular structure, marked in FIG. 1 by asterisks ("*"). Each chiral carbon has two possible configurations, R or S, so the presence of three chiral carbons means that there are eight distinct stereoisomers (RRR, SSS, RSR, SRS, etc.) of the tocopherol molecule. Natural Vitamin E is a single stereoisomer, RRR-alpha-tocopherol, whereas synthetic vitamin E (all-rac-alpha-tocopherol) is an equimolar mixture of all eight isomers, only one of which is RRR-alpha tocopherol. As previously discussed, RRR-alpha-tocopherol has the greatest biological activity of the stereoisomers, and is reported to be the dominant form of alpha-tocopherol in the brain.

Tocopherols are powerful antioxidants which scavenge reactive oxygen species and free radicals before these oxidants can cause damage in living cells. Tocopherols are particularly useful since they are lipophilic and therefore can protect the fatty structures of a cell, such as the cell wall, from oxidative damage. As discussed above, alpha-tocopherol is thought to prevent or lessen many medical and biological problems associated with oxidative stress. During pregnancy, oxidative stress and damage are associated with problems such as low birth weight and preterm delivery. In addition to its antioxidant properties, alpha-tocopherol is thought to reduce inflammation and enhance the release of prostacyclin in the mother. Prostacyclin inhibits platelet aggregation and increases vasodilation, thereby regulating both the blood flow between the placenta and fetus and the blood flow within the fetus. Increasing maternal blood flow also increases the nutrient supply to the fetus, leading to proper fetal growth. Inadequate levels of prostacyclin can lead to vasoconstriction, which may contribute to preeclampsia in the mother and inadequate blood flow and nutrient supply to the fetus.

Tocopherols are prone to reaction and degradation over time, particularly when purified and stored long-term. Tocopherol esters are more stable for long-term storage, and so tocopherols used in nutritional compositions and to fortify processed foods are often in the form of tocopherol acetate or tocopherol succinate. Once ingested, however, tocopherol esters are quickly converted back to free tocopherol in the digestive tract.

It has long been known that the stereoisomers of alpha-tocopherol differ in their biological activity, with RRR-alpha-tocopherol being the most biologically active form. Accepted nutritional guidelines hold that RRR-alpha-tocopherol is 1.36 times more biologically active than all-rac-alpha-tocopherol. Recent studies have indicated that the biological activity of RRR-alpha-tocopherol may actually be even higher, perhaps about 2 times the activity of all-rac-alpha-tocopherol. This difference in biological activity is not because RRR-alpha-tocopherol is intrinsically a better antioxidant than the non-RRR-alpha-tocopherol stereoisomers. In vitro studies have shown that all stereoisomers of alpha-tocopherol are equally reactive with oxidative chemicals such as peroxide. Instead, it appears that RRR-alpha-tocopherol is more bioavailable than the other stereoisomers. Compared to the SXX-alpha-tocopherol stereoisomers, the four RXX-alpha-tocopherol stereoisomers are preferentially transferred from the liver into very-low-density lipoproteins (VLDL), and then into plasma and red blood cells. Once in the bloodstream, other organs such as the brain preferentially absorb the RRR-alpha-tocopherol stereoisomer. Hence, certain metabolic systems of the human body actively and preferentially absorb RRR-alpha-tocopherol over the non-RRR-alpha-tocopherol stereoisomers present in all-rac-alpha-tocopherol.

Although the human body prefers RRR-alpha-tocopherol over the non-RRR-alpha-tocopherol stereoisomers, the non-RRR-alpha-tocopherol stereoisomers in all-rac-alpha-tocopherol have typically been considered beneficial. Non-RRR-alpha-tocopherol stereoisomers have typically been thought to provide antioxidant capacity and health benefits which, though less biologically active, are similar to the benefits provided by the RRR-alpha-tocopherol stereoisomer in all-rac-alpha-tocopherol. All-rac-alpha-tocopherol is also less expensive than RRR-alpha-tocopherol. For these reasons, all-rac-alpha-tocopherol is often used as a dietary supplement, both alone and in multivitamins. All-rac-alpha-tocopherol is also used to fortify many processed foods, such as breakfast cereals. Therefore, people may regularly consume all-rac-alpha-tocopherol, even if they do not specifically choose to take supplemental Vitamin E in capsules or multivitamins. When all-rac-alpha-tocopherol is used as a supplement or fortifier, the dosage is typically increased to compensate for the lower activity of the non-RRR-alpha-tocopherol stereoisomers.

It is known that RRR-alpha-tocopherol is more biologically active than all-rac-RRR-alpha-tocopherol. It is also known that rodent brain exerts additional selectivity for RRR-alpha-tocopherol as compared to non-RRR-alpha-tocopherol stereoisomers. However, it has been unclear if bio-selectivity of alpha-tocopherol stereoisomers occurs in human infant brains.

Carotenoids

Carotenoids are a class of chemicals that are organic pigments found in plants. Carotenoids are responsible for the bright red, yellow, and orange colors in many vegetables and fruits. Carotenoids absorb light energy and provide antioxidant properties to plants that produce them and animals that consume them. Some carotenoids are converted to Vitamin A, which is essential to vision and normal growth.

All carotenoids are tetraterpenoids, meaning they are produced from eight isoprene molecules. All carotenoids therefore contain 40 carbon atoms. Examples of carotenoids include α-carotene, β-carotene, γ-carotene, lycopene, lutein, zeaxanthin, astaxanthin, α-cryptoxanthin, β-cryptoxanthin, and similar chemicals. Carotenoids contain many conjugated double bonds which absorb visible light, which causes the pigmentation of the carotenoid compounds. These carotenoid pigments are responsible for some of the colors of fall foliage, once the green chlorophyll (which masks the carotenoid pigments) fades from dying leaves.

Carotenoids appear to decrease the risk of disease in humans, particularly certain cancers and eye diseases, through their role as antioxidants. Lutein and zeaxanthin, for example, are found in the retina of the eye, and it is thought that these carotenoids may slow the development of age-related eye diseases. Carotenoids are fat-soluble compounds, with little or no water solubility. To absorb ingested carotenoids, humans and animals should consume the carotenoid-containing food or vitamin supplement with a meal containing fat.

Accumulation of RRR-Alpha-Tocopherol in Occipital Cortex

The inventors have unexpectedly discovered that RRR-alpha-tocopherol is preferentially accumulated in the brain of infants, and specifically in the occipital cortex of infants. This area of the brain is the area of the brain important for processing visual information. The preferential accumulation of RRR-alpha-tocopherol in the occipital cortex is thought to be important to the development of visual processing, visual acuity, or both in an infant. The preferential accumulation of RRR-alpha-tocopherol in the occipital cortex is also thought to be important to supporting visual processing, visual acuity, or both in an infant.

The inventors have also unexpectedly discovered that carotenoids selectively reduce the accumulation of non-RRR-alpha-tocopherol in the occipital cortex of infants' brains, but not in other areas of the brain, such as the frontal cortex or hippocampus.

By administering a nutritional composition comprising RRR-alpha-tocopherol (instead of all-rac-alpha-tocopherol) and a carotenoid, the concentration of RRR-alpha-tocopherol in the occipital cortex of the infant's developing brain is enhanced and the concentration of non-RRR-alpha-tocopherol is reduced. By enhancing the concentration of RRR-alpha-tocopherol and reducing the concentration of non-RRR-alpha-tocopherol in the occipital cortex of an infant's brain, it is thought that the visual processing, visual acuity, or both in the infant can be improved. By enhancing the concentration of RRR-alpha-tocopherol in the occipital cortex of an infant's brain, it is thought that the development of visual processing, visual acuity, or both is enhanced in an infant. In other words, the increase in concentration of the RRR-alpha-tocopherol in the occipital cortex results in improved development of visual processing, visual acuity, or both in the infant.

The bioavailability and absorption of RRR-alpha-tocopherol that has been added to the present nutritional compositions may be determined by extracting alpha-tocopherol from tissue samples (e.g., brain tissue samples) and analyzing the extract by high-performance liquid chromatography (HPLC). The extracts may be analyzed using an HPLC analysis method that is able to separate and quantify the individual stereoisomers of alpha-tocopherol.

The concentration of various carotenoid compounds (e.g., β-carotene, lycopene, lutein, zeaxanthin, etc.) in tissue samples may also be determined by extracting the carotenoid(s) from the tissue samples and analyzing the extracts by HPLC.

Product Form

In some embodiments, the nutritional compositions of the present disclosure comprise RRR-alpha-tocopherol and a carotenoid. In some embodiments, the nutritional compositions of the present disclosure comprise RRR-alpha-tocopherol. Non-limiting examples of nutritional compositions of the present disclosure include nutritional compositions intended for oral consumption. In some embodiments, suitable forms for the nutritional compositions may include nutritional food or beverage products, such as milk- or soy-based beverages, mix-in powders for beverages, infant cereal products, etc. In some embodiments, the nutritional compositions of the present disclosure are infant nutritional formulas. In some embodiments, suitable forms for the nutritional compositions may include medicine-like forms, such as tablets, capsules, chewable soft gels, syrups, and elixirs.

The nutritional compositions according to the present disclosure may include RRR-alpha-tocopherol in any amount that is sufficient for the intended purpose. In some embodiments, the amount of RRR-alpha-tocopherol supplied by the nutritional composition is from about 0.5 mg to about 100 mg of RRR-alpha-tocopherol per day. In other embodiments, the amount of RRR-alpha-tocopherol supplied by the nutritional composition is from about 1 mg to about 75 mg of RRR-alpha-tocopherol per day, including from about 2 mg to about 60 mg, including from about 3 mg to about 50 mg, including from about 4 mg to about 40 mg, including from about 5 mg to about 30 mg, including from about 6 mg to about 25 mg, including from about 7 mg to about 20 mg, including from about 8 mg to about 15 mg, and including from about 9 mg to about 10 mg of RRR-alpha-tocopherol per day.

The nutritional compositions according to the present disclosure may include at least one carotenoid in any amount that is sufficient for the intended purpose. In some embodiments, the carotenoid comprises β-carotene. A preferred amount of β-carotene supplied by the nutritional composition is from about 5 μg to about 160 mg of β-carotene per day, including from about 10 μg to about 140 mg, including from about 20 μg to about 100 mg, including from about 40 μg to about 80 mg, including from about 50 μg to about 60 mg, of β-carotene per day. In some embodiments, the carotenoid comprises lycopene. A preferred amount of lycopene supplied by the nutritional composition is from about 1.4 μg to about 180 mg of lycopene per day, including from about 4 μg to about 120 mg, including from about 6 μg to about 80 mg, including from about 10 μg to about 60 mg, including from about 20 μg to about 40 mg, of lycopene per day. In some embodiments, the carotenoid comprises lutein. A preferred amount of lutein supplied by the nutritional composition is from about 1 μg to about 240 mg of lutein per day, including from about 5 μg to about 200 mg, including from about 10 μg to about 150 mg, including from about 20 μg to about 100 mg, including from about 50 μg to about 75 mg, of lutein per day. In some embodiments, the carotenoid comprises zeaxanthin. A preferred amount of zeaxanthin supplied by the nutritional composition is from about 1 μg to about 180 mg of zeaxanthin per day, including from about 5 µg to about 140 mg, including from about 10 µg to about 100 mg, including from about 20 µg to about 60 mg, including from about 30 µg to about 50 mg, of zeaxanthin per day. In some embodiments, the carotenoid comprises α-carotene. A preferred amount of α-carotene supplied by the nutritional composition is from about 1 µg to about 180 mg of α-carotene per day, including from about 5 µg to about 140 mg, including from about 10 µg to about 100 mg, including from about 20 µg to about 60 mg, including from about 30 µg to about 50 mg, of α-carotene per day. In some embodiments, the carotenoid comprises α-cryptoxanthin. A preferred amount of α-cryptoxanthin supplied by the nutritional composition is from about 0.5 µg to about 90 mg of α-cryptoxanthin per day, including from about 1 µg to about 75 mg, including from about 5 µg to about 50 mg, including from about 10 µg to about 30 mg, including from about 20 µg to about 15 mg, of α-cryptoxanthin per day. In some embodiments, the carotenoid comprises a mixture of two or more carotenoids in amounts that are sufficient for the intended purpose.

Macronutrients

Nutritional compositions according to the present disclosure may comprise one or more macronutrients selected from the group consisting of fat, protein, carbohydrate, and mixtures thereof. This is particularly true for nutritional compositions that are in the form of nutritional food or beverage products. Generally, any source of fat, carbohydrate, or protein that is suitable for use in nutritional food or beverage products is also suitable for use herein, provided that such macronutrients are also compatible with the essential elements of the nutritional compositions as defined herein.

Although total concentrations or amounts of fat, protein, and carbohydrates may vary depending upon the nutritional needs of the subject, such concentrations or amounts most typically fall within one of the following embodied ranges, inclusive of any other essential fat, protein, and or carbohydrate ingredients as described herein.

Carbohydrate concentrations may typically range from about 5 wt % to about 70 wt %, including from about 7 wt % to about 60 wt %, including from about 10 wt % to about 55 wt %, by weight of the nutritional composition. Fat concentrations most typically range from about 0.5 wt % to about 35 wt %, including from about 0.75 wt % to about 30 wt %, including from about 1 wt % to about 28 wt %, and also including from about 2 wt % to about 5 wt %, by weight of the nutritional composition. Protein concentrations may range from about 1 wt % to about 85 wt %, from about 5 wt % to about 50 wt %, from about 7 wt % to about 32 wt %, or from about 8 wt % to about 30 wt %, by weight of the nutritional composition. Additional ranges for carbohydrates, fats, and proteins, based on percent of calories of the nutritional composition, are set forth in Table 2.

TABLE 2

| Macronutrient | Embodiment A (% Calories) | Embodiment B (% Calories) | Embodiment C (% Calories) |
| --- | --- | --- | --- |
| Carbohydrate | 1-98 | 0-75 | 30-50 |
| Fat | 1-98 | 20-70 | 35-40 |
| Protein | 1-98 | 5-85 | 15-85 |

Note:
Each numerical value in the table is preceded by the term "about."

Non-limiting examples of suitable fats in the nutritional compositions described herein may be selected from the group of coconut oil, fractionated coconut oil, soy oil, corn oil, olive oil, safflower oil, high oleic safflower oil, medium chain triglyceride oil, sunflower oil, high oleic sunflower oil, palm and palm kernel oils, palm olein, canola oil, walnut oil, flaxseed oil, marine oils, cottonseed oil, borage oil, algal oils, fungal oils, and combinations thereof. It should be noted that fats and oil typically contain RRR-alpha-tocopherol naturally. For the purposes of this disclosure, the RRR-alpha-tocopherol contributed by any fats or oils in the nutritional compositions described herein should be considered as part of the RRR-alpha-tocopherol component of the ATC for the purpose of calculating the RRR-alpha-tocopherol to non-RRR-alpha-tocopherol weight ratio.

Non-limiting examples of suitable carbohydrates or sources thereof in the nutritional compositions may be selected from the group of maltodextrin, hydrolyzed or modified starch or cornstarch, glucose polymers, corn syrup, corn syrup solids, rice-derived carbohydrates, sucrose, glucose, fructose, lactose, high fructose corn syrup, honey, sugar alcohols (e.g., maltitol, erythritol, or sorbitol), and combinations thereof.

Non-limiting examples of suitable protein or sources thereof in the nutritional compositions may be selected from the group of partially hydrolyzed or non-hydrolyzed proteins derived from any suitable source, such as milk (e.g., casein or whey), animal (e.g., meat or fish), cereal (e.g., rice or wheat), vegetable (e.g., pea, potato, or bean), or combinations thereof. Non-limiting examples of such proteins include whole cow's milk, partially or completely defatted milk, milk protein isolates, milk protein concentrates, caseinates, casein protein isolates, whey protein, whey protein concentrates, soy protein isolates, soy protein concentrates, pea protein isolates, pea protein concentrates, hydrolyzed yeast, potato, rice, wheat, canola, animal collagen, gelatin, bovine colostrum, human colostrum, glycomacropeptides, mycoproteins, amino acids, and combinations thereof.

In some embodiments, the nutritional compositions include a protein component that consists of only intact or partially hydrolyzed protein; that is, the protein component is substantially free of any protein that has a degree of hydrolysis of 25% or more. In this context, the term "partially hydrolyzed protein" refers to proteins having a degree of hydrolysis of less than 25%, including less than 20%, including less than 15%, including less than 10%, and including proteins having a degree of hydrolysis of less than 5%. The degree of hydrolysis is the extent to which peptide bonds are broken by a hydrolysis chemical reaction. To quantify the partially hydrolyzed protein component of these embodiments, the degree of protein hydrolysis is determined by quantifying the amino nitrogen to total nitrogen ratio (AN/TN) of the protein component of the selected composition. The amino nitrogen component is quantified by USP titration methods for determining amino nitrogen content, while the total nitrogen component is determined by the Tecator® Kjeldahl method. These analytical methods are well known.

Optional Ingredients

The nutritional compositions described herein may further comprise other optional ingredients that may modify the physical, chemical, hedonic, or processing characteristics of the compositions or serve as additional nutritional components. Many such optional ingredients are known or otherwise suitable for use in other nutritional products and may also be used in the compositions described herein, provided that such optional ingredients are safe and effective for oral administration and are compatible with the essential and other ingredients in the selected product form.

Non-limiting examples of such optional ingredients include preservatives, antioxidants, emulsifying agents, buffers, additional nutrients as described herein, colorants, flavors, thickening agents, stabilizers, and so forth.

The compositions may further comprise minerals, non-limiting examples of which include calcium, phosphorus, magnesium, iron, zinc, manganese, copper, sodium, potassium, molybdenum, chromium, selenium, chloride, and combinations thereof.

The compositions may further comprise vitamins or related nutrients, non-limiting examples of which include vitamin A, vitamin C, vitamin D, vitamin K, thiamine, riboflavin, pyridoxine, vitamin B12, niacin, folic acid, pantothenic acid, biotin, inositol, salts and derivatives thereof, and combinations thereof.

In some embodiments, the compositions may comprise a compound selected from the group of choline, arachidonic acid, eicosapentaenoic acid, docosahexaenoic acid, and combinations thereof.

The compositions may also include one or more masking agents to reduce or otherwise obscure bitter flavors and after taste. Suitable masking agents include natural and artificial sweeteners, sodium sources such as sodium chloride, and hydrocolloids, such as guar gum, xanthan gum, carrageenan, gellan gum, and combinations thereof. The amount of masking agent in the composition may vary depending upon the particular masking agent selected, other ingredients in the nutritional composition, and other product target variables. Such amounts, however, most typically range from at least 0.1 wt %, including from about 0.15 wt % to about 3.0 wt %, and also including from about 0.18 wt % to about 2.5 wt %, by weight of the nutritional composition.

Methods of Use

The methods described herein improve the visual processing, visual acuity, or both in healthy infants by administering nutritional compositions comprising RRR-alpha-tocopherol and a carotenoid to the infants. The methods described herein also improve the visual processing, visual acuity, or both in healthy infants by administering nutritional compositions comprising RRR-alpha-tocopherol to the infants. The methods described herein also improve the development of an infant's occipital cortex to enhance the developing visual processing, visual acuity, or both in the infant.

In some embodiments, the nutritional compositions comprise RRR-alpha-tocopherol in the form of an RRR-alpha-tocopherol ester. In some embodiments, the nutritional compositions comprise a carotenoid selected from α-carotene, β-carotene, γ-carotene, lycopene, lutein, zeaxanthin, astaxanthin, α-cryptoxanthin, β-cryptoxanthin, and combinations thereof.

In some embodiments, the methods improve the visual processing, visual acuity, or both, of premature infants. In some embodiments, the methods improve the visual processing, visual acuity, or both, of full-term infants. In some embodiments, the methods improve the visual processing, visual acuity, or both, of infants who do not have an ocular disease. In some embodiments, the methods improve the development of the visual processing, visual acuity, or both, in premature infants. In some embodiments, the methods improve the development of the visual processing, visual acuity, or both, in full-term infants. In some embodiments, the methods improve the development of the visual processing, visual acuity, or both, in infants who do not have an ocular disease.

The following examples illustrate specific embodiments and specific features of the present invention. The examples are given solely for the purpose of illustration and are not to be construed as a limitation of the present disclosure, as many variations thereof are possible without departing from the spirit and scope of the disclosure.

EXAMPLES

Example 1

In Example 1, the brain tissues of infants were sampled to measure the concentration of total alpha-tocopherol and RRR-alpha-tocopherol.

Subjects were infants (n=25) who died during the first year of life from either SIDS or other conditions. Brain tissues (occipital cortex, OC {n=17}; frontal cortex, FC {n=17}; and hippocampus, HPC {n=19}) from the NICHD Brain and Tissue Bank were processed using standard lipid extraction procedures and analyzed using chiral reverse phase HPLC. Data are presented as concentrations (μg/g tissue) of total alpha-tocopherol or RRR-alpha-tocopherol in the brain tissue.

Figure 2:
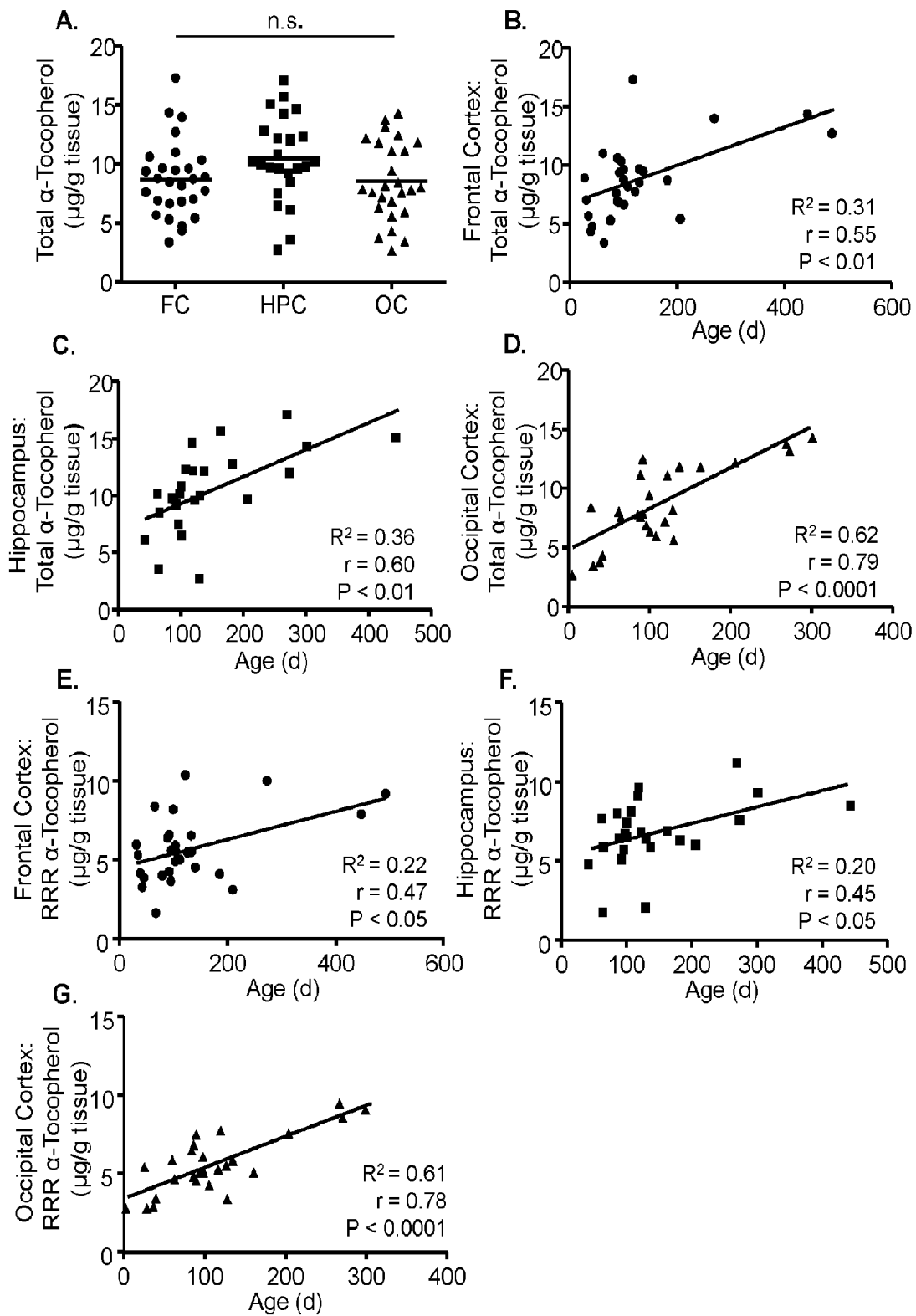
FIG. 2 is a series of graphs showing the concentration of total alpha-tocopherol and RRR-alpha-tocopherol in various areas of infant brain tissues as the infants age.

FIG. 2 illustrates the total alpha-tocopherol and RRR-alpha-tocopherol measured in human infant brain tissues. All samples analyzed contained detectable concentrations of alpha-tocopherol. Specifically, graph A shows the total alpha-tocopherol concentrations for tissues from the frontal cortex (FC), hippocampus (HPC), and occipital cortex (OC). The mean concentration in each region is denoted by a horizontal bar. The data demonstrate that the mean concentration of total alpha-tocopherol was similar in the FC (9.71 μg/g), OC (8.74 μg/g), and HPC (11.64 μg/g). No differences were detected among brain regions ("n.s." means "not significant.") These data show that total alpha-tocopherol concentration was similar in all brain regions analyzed. In addition, total alpha-tocopherol was analyzed by age (in days) in the frontal cortex (graph B), hippocampus (graph C), and occipital cortex (graph D). These data reveal that total alpha-tocopherol concentration increased with age in human infant brain. RRR-alpha-tocopherol concentrations were also measured in the frontal cortex (graph E), hippocampus (graph F), and occipital cortex (graph G) of human infant brain tissues and reported as a function of age.

It was found that RRR-alpha-tocopherol is the predominant stereoisomer in all samples and brain regions analyzed, compared to all non-RRR-alpha-tocopherol stereoisomers ($P<0.0001$). Specifically, the mean concentration of RRR-alpha-tocopherol was 6.4 μg/g in the FC, 5.7 μg/g in the OC, and 7.6 μg/g in the HPC. Furthermore, the ratio of the mean concentration of RRR-alpha-tocopherol to the mean total concentration of the non-RRR-alpha-tocopherol stereoisomers was 2.4:1, 2.3:1, and 2.3:1 in the FC, OC, and HPC, respectively.

Unexpectedly, a strong correlation between age and mean concentration of both RRR-alpha-tocopherol and total alpha-tocopherol was observed, but only in the occipital cortex (graphs D and G), while lesser relationships of this nutrient with development occurred in other brain regions. This preferential accumulation in the occipital cortex, the region of the brain responsible for visual processing of information, suggests that RRR-alpha-tocopherol plays an important role in visual processing and acuity.

Example 2

Figure 3:
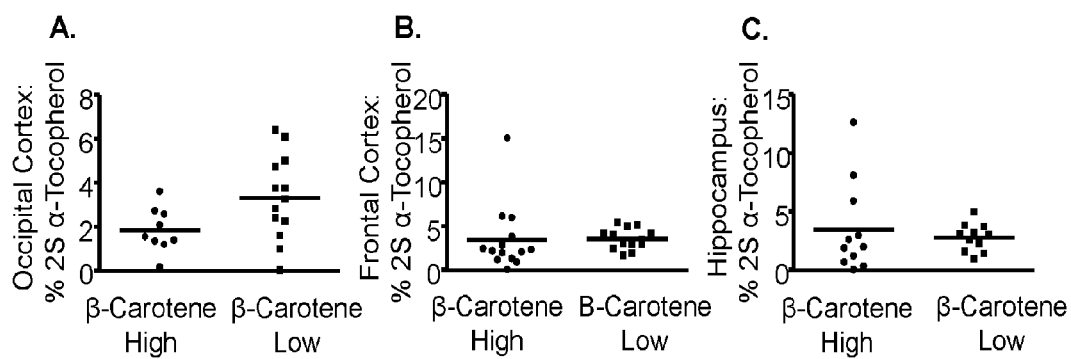
FIG. 3 is a series of graphs showing the percentage of 2S-alpha-tocopherol in various areas of infant brain tissues, grouped as also containing either high or low concentrations of β-carotene.

In Example 2, the brain tissues of Example 1 were analyzed by HPLC to determine the concentration of β-carotene in the OC, FC, and HPC regions. The individual samples from each region were stratified according to their median β-carotene concentration into "β-carotene high" and "β-carotene low" groups. The percentage of the 2S-alpha-tocopherol (based on total alpha-tocopherol detected) in each sample from the OC (graph A), the FC (graph B) and the HPC (graph C) was plotted for the "high" and "low" β-carotene groups, as shown in FIG. 3.

For the FC and HPC tissues, the mean 2S-alpha-tocopherol percentages were not significantly different between the "high" and "low" β-carotene groups. However, it was surprisingly discovered that, in the OC tissues (graph A), the mean 2S-alpha-tocopherol percentage was significantly less in the "high" β-carotene group when compared to the "low" β-carotene group (p<0.05).

These results indicate that infant brains containing higher concentrations of β-carotene correlate with reduced levels of 2S-alpha-tocopherol in the occipital cortex. Conversely, infant brains containing lower concentrations of β-carotene correlate with higher levels of 2S-alpha-tocopherol in the occipital cortex. This suggests that increasing the amount of β-carotene available to an infant during the first years of life may increase the concentration of β-carotene in the occipital cortex, reduce the uptake of 2S-alpha-tocopherol, and enhance the preferential accumulation of RRR-alpha-tocopherol in the occipital cortex. The preferential accumulation of RRR-alpha-tocopherol in the occipital cortex suggests that RRR-alpha-tocopherol plays an important role in visual processing and acuity.

Example 3

Figure 4:
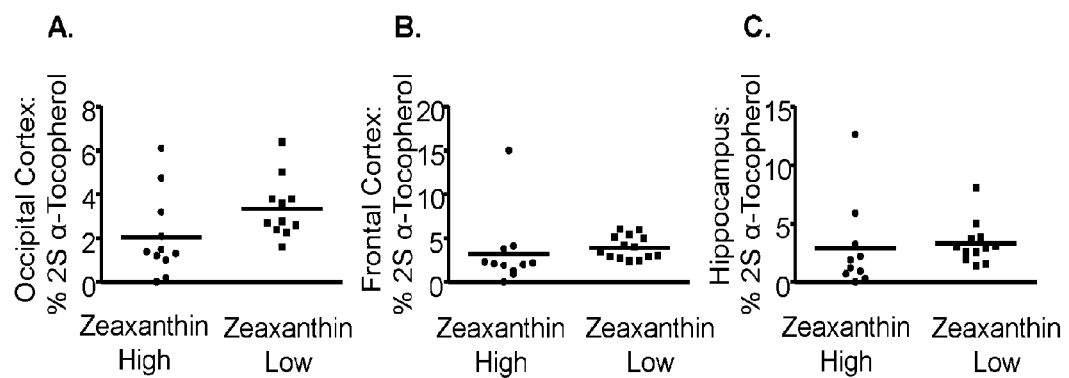
FIG. 4 is a series of graphs showing the percentage of 2S-alpha-tocopherol in various areas of infant brain tissues, grouped as also containing either high or low concentrations of zeaxanthin.

In Example 3, the brain tissues of Example 1 were analyzed by HPLC to determine the concentration of zeaxanthin in the OC, FC, and HPC regions. The individual samples from each region were stratified according to their median zeaxanthin concentration into "zeaxanthin high" and "zeaxanthin low" groups. The percentage of 2S-alpha-tocopherol (based on total alpha-tocopherol detected) in each sample from the OC (graph A), the FC (graph B) and the HPC (graph C) was plotted for the "high" and "low" zeaxanthin groups, as shown in FIG. 4.

For the FC and HPC tissues, the mean 2S-alpha-tocopherol percentages were not significantly different between the "high" and "low" zeaxanthin groups. However, it was surprisingly discovered that, in the OC tissues (graph A), the mean 2S-alpha-tocopherol percentage showed a trend of less in the "high" zeaxanthin group when compared to the "low" zeaxanthin group (p=0.08).

These results indicate that infant brains containing higher concentrations of zeaxanthin correlate with reduced levels of 2S-alpha-tocopherol in the occipital cortex. Conversely, infant brains containing lower concentrations of zeaxanthin correlate with higher levels of 2S-alpha-tocopherol in the occipital cortex. This suggests that increasing the amount of zeaxanthin available to an infant during the first years of life may increase the concentration of zeaxanthin in the occipital cortex, reduce the uptake of 2S-alpha-tocopherol, and enhance the preferential accumulation of RRR-alpha-tocopherol in the occipital cortex. The preferential accumulation of RRR-alpha-tocopherol in the occipital cortex suggests that RRR-alpha-tocopherol plays an important role in visual processing and acuity.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative compositions and methods, and illustrative examples shown and described. Accordingly, departures may be made from such details without departing from the spirit or scope of the applicant's general disclosure herein.

What is claimed is:

1. A method of improving the visual processing of a healthy infant, the method comprising administering a nutritional composition comprising RRR-alpha-tocopherol and a carotenoid to the infant.

2. The method of claim 1 wherein the carotenoid is selected from the group consisting of α-carotene, β-carotene, γ-carotene, lycopene, lutein, zeaxanthin, astaxanthin, α-cryptoxanthin, β-cryptoxanthin, and combinations thereof.

3. The method of claim 1 wherein the nutritional composition delivers about 0.5 mg to about 100 mg RRR-alpha-tocopherol per day to the infant, and wherein the carotenoid is selected from the group consisting of:
   a) β-carotene, and the nutritional composition delivers about 5 µg to about 160 mg β-carotene per day to the infant;
   b) lycopene, and the nutritional composition delivers about 1.4 µg to about 180 mg lycopene per day to the infant;
   c) lutein, and the nutritional composition delivers about 1 µg to about 240 mg lutein per day to the infant;
   d) zeaxanthin, and the nutritional composition delivers about 1 µg to about 180 mg zeaxanthin per day to the infant;
   e) α-carotene, and the nutritional composition delivers about 1 µg to about 180 mg α-carotene per day to the infant;
   f) α-cryptoxanthin, and the nutritional composition delivers about 0.5 µg to about 90 mg α-cryptoxanthin per day to the infant; and
   g) combinations thereof.

4. The method of claim 1 wherein the nutritional composition is an infant nutritional formula comprising about 2% to about 75% protein, about 1% to about 85% carbohydrate, and about 5% to about 70% fat as percentages of the total calories.

5. The method of claim 1 wherein the nutritional composition is a vitamin composition.

6. The method of claim 5 wherein the vitamin composition is in a form selected from the group consisting of tablets, chewable tablets, capsules, powders, aqueous liquids, oil-based liquids, slurries, syrups, elixirs, and combinations thereof.

7. The method of claim 5 wherein the vitamin composition further comprises at least one of Vitamin A, Vitamin D, Vitamin K, Coenzyme $Q_{10}$, α-linolenic acid, arachidonic acid, eicosapentaenoic acid, docosahexaenoic acid, and combinations thereof.

8. The method of claim 1 wherein the infant is a premature infant or wherein the infant does not have ocular disease.

9. A method of improving the visual acuity of a healthy infant, the method comprising administering a nutritional composition comprising RRR-alpha-tocopherol and a carotenoid to the infant.

10. The method of claim 9 wherein the nutritional composition delivers about 0.5 mg to about 100 mg RRR-alpha-tocopherol per day to the infant, and wherein the carotenoid is selected from the group consisting of:

a) β-carotene, and the nutritional composition delivers about 5 μg to about 160 mg β-carotene per day to the infant;
b) lycopene, and the nutritional composition delivers about 1.4 μg to about 180 mg lycopene per day to the infant;
c) lutein, and the nutritional composition delivers about 1 μg to about 240 mg lutein per day to the infant;
d) zeaxanthin, and the nutritional composition delivers about 1 μg to about 180 mg zeaxanthin per day to the infant;
e) α-carotene, and the nutritional composition delivers about 1 μg to about 180 mg α-carotene per day to the infant;
f) α-cryptoxanthin, and the nutritional composition delivers about 0.5 μg to about 90 mg α-cryptoxanthin per day to the infant; and
g) combinations thereof.

11. The method of claim 9 wherein the nutritional composition is an infant nutritional formula comprising about 2% to about 75% protein, about 1% to about 85% carbohydrate, and about 5% to about 70% fat as percentages of the total calories.

12. The method of claim 9 wherein the nutritional composition is a vitamin supplement.

13. The method of claim 12 wherein the vitamin supplement is in a form selected from the group consisting of tablets, chewable tablets, capsules, powders, aqueous liquids, oil-based liquids, slurries, syrups, elixirs, and combinations thereof.

14. The method of claim 12 wherein the vitamin supplement further comprises at least one of Vitamin A, Vitamin D, Vitamin K, Coenzyme $Q_{10}$, α-linolenic acid, arachidonic acid, eicosapentaenoic acid, docosahexaenoic acid, and combinations thereof.

15. The method of claim 9 wherein the nutritional composition is administered at least once per day.

16. The method of claim 9 wherein the infant is a premature infant.

17. The method of any claim 9 wherein the infant does not have ocular disease.

18. The method of claim 9 wherein the carotenoid is selected from the group consisting of α-carotene, β-carotene, γ-carotene, lycopene, lutein, zeaxanthin, astaxanthin, α-cryptoxanthin, β-cryptoxanthin, and combinations thereof.

19. A method of improving the development of both visual processing and visual acuity in an infant, the method comprising administering a nutritional composition comprising RRR-alpha-tocopherol and a carotenoid to the infant, wherein the carotenoid is selected from the group consisting of α-carotene, β-carotene, γ-carotene, lycopene, lutein, zeaxanthin, astaxanthin, α-cryptoxanthin, β-cryptoxanthin, and combinations thereof.

* * * * *